United States Patent
Bergström et al.

(12)

(10) Patent No.: US 6,294,706 B1
(45) Date of Patent: Sep. 25, 2001

(54) METHOD FOR PREPARING NORBORNENE AND SUBSTITUTED DERIVATIVES OF NORBORNENE

(75) Inventors: Christer Bergström; Jukka Koskinen, both of Espoo; Erkki Halme, Helsinki; Matti Lindström; Mika Perälä, both of Lappeenranta, all of (FI)

(73) Assignee: Opatatech Corporation, Espoo (FI)

( * ) Notice: Subject to any disclaimer, the term of this patent is extended or adjusted under 35 U.S.C. 154(b) by 0 days.

(21) Appl. No.: 09/142,806

(22) PCT Filed: Mar. 13, 1997

(86) PCT No.: PCT/FI97/00169

§ 371 Date: Oct. 29, 1998

§ 102(e) Date: Oct. 29, 1998

(87) PCT Pub. No.: WO97/33848

PCT Pub. Date: Sep. 18, 1997

(30) Foreign Application Priority Data

Mar. 13, 1996 (FI) .................................................. 961184

(51) Int. Cl.$^7$ ...................................................... C07C 2/50
(52) U.S. Cl. ............................. 585/361; 585/354; 526/75
(58) Field of Search ..................................... 585/361, 502, 585/354; 556/466, 489; 526/75, 281, 283

(56) References Cited

U.S. PATENT DOCUMENTS

| 3,919,356 | * | 11/1975 | Boyer ..................................... 524/405 |
| 4,532,297 |   | 7/1985 | Gardner . |
| 5,095,082 | * | 3/1992 | Kelsey .............................. 585/361 X |
| 5,138,003 | * | 8/1992 | Okumura et al. .................. 526/75 X |
| 5,457,249 | * | 10/1995 | Toshihiro et al. ............... 528/281 X |

* cited by examiner

*Primary Examiner*—Fred Teskin
(74) *Attorney, Agent, or Firm*—Cohen, Pontani, Lieberman & Pavane

(57) ABSTRACT

Disclosed is a method for the preparation of norbornene and substituted norbornene compounds via a Diels-Alder reaction, in which a cyclic diene is reacted with an olefinic compound in order to prepare a norbornene compound. According to the invention a cyclic diene is gradually added to react with an olefinic compound, in order to keep the concentration of the cyclic diene in the reaction mixture as low as possible during the reaction. It is possible to obtain a very pure product, high yield, short reaction time and high concentrations of the exo diastereomer with the method of the invention.

19 Claims, No Drawings

METHOD FOR PREPARING NORBORNENE AND SUBSTITUTED DERIVATIVES OF NORBORNENE

BACKGROUND OF THE INVENTION

The present invention relates to a method for preparing norbornene and substituted derivatives of norbornene via the Diels-Alder reaction.

The described method comprises reacting a cyclic diene with an olefinic compound to yield norbornene or a substituted derivative of norbornene.

The present invention also relates to a polymer prepared by polymerizing a monomer prepared by the method of the invention in the presence of a catalyst and another monomer.

Norbornene and substituted norbornene compounds are used for the preparation of such compounds as cycloolefine-copolymers (COC). These copolymers may be prepared, for example, by introducing a norbornene derivative in a metathesis-ring-opening polymerization reaction or reacting norbornene with ethene or an other alpha-olefine in the presence of a vanadine based Ziegler-Natta catalyst or a metallocene catalyst.

It is essential in all of these polymerization reactions that the cyclic monomer is pure. Especially polyunsaturated impurities (such as the trimer or dimer of cyclopentadiene) are adverse, because they cause cross-linking in polymers. Other polycyclic impurities (such as tetracyclododecene compounds) may also have adverse effects, because they cause polymer chains to be of greater rigidity than norbornene and substituted norbornene compounds, thereby causing the properties of the polymers to be prepared to become different from those achieved when pure products are used for polymerization. Furthermore, it should be pointed out that the diastereomers (exo and endo forms, respectively) of norbornene compounds have a different effect on polymer compounds; the exo form yields more rigid polymers than the endo form. From the point of view of further use of the monomer, the product should contain as much as possible of the desired diastereomer. Usually, one attempts to achieve as high as possible a concentration of the exo diastereomer.

Because mixtures of cycloolefin compounds are difficult to purify by distillation, it is preferable to synthesize them under conditions, in which the desired norbornene or substituted cylcoolefin compound (the endo or exo diastereomer of substituted norbornene or the corresponding tetracyclododecene compound) are in as pure a form as possible.

Among the substituted norbornene derivatives, e.g. phenylnorbornene (5-phenyl-bicyclo-[2.2.1]-hept-2-ene) and indanylnorbornene (1,4-methano-1,9a,4,4a-tetrahydrofluorene) are known organic compounds. They have been prepared in a batch process by using a solvent and starting compounds in equimolar ratios. This requires a very long reaction time if a high yield and a pure product are desired. Elevation of the reaction temperature can be used to shorten the reaction time, but at the same time the product yielded turns out to be very impure (the reaction mixture contains large amounts of the trimer and tetracyclododecene compounds). On the other hand, maintaining a low temperature and extending the reaction time causes the undesired endo form to become the predominating diastereomer.

Some solutions to these problems have been suggested in the known art. Nippon Zeon has performed the synthesis of phenylnorbornene by using a large excess of styrene as the solvent (EP-A2-0 345 674) and Mitsui Sekka has developed a method for the isomerisation of the endo diastereomer into the exo diastereomer (EP-A1-0 499 226). It is not possible to use these methods either for the preparation of pure products with high yields.

DE Published Patent Application No. 2 161 215 discloses a process for preparing 5-vinylnorbornene-2. According to this known process cyclopentadiene is slowly added to a mixture of butadien and di-tert-butyl-p-cresol. The reaction is interrupted after 60 minutes, when 20% of the cyclopentadiene has reacted. The yield of vinylnorbornene is only 71.6% and the reaction mixture obtained is rather impure containing a mixture of cyclopentadien, dicyclopentadien, butadiene, 5-vinylnorbornene-2 bicyclonoadiene, vinylcyclohexene and residues with higher boiling points.

The object of the present invention is to overcome the shortcomings of known techniques and to provide an entirely new method for the preparation of norbornene and substituted norbornene derivatives.

The invention is based on the idea of synthesizing norbornene compounds via a Diels-Alder reaction while maintaining a low or relatively low concentration of the cyclic diene. According to the invention, this is achieved by introducing a cyclic diene into the reaction with an olefinic compound gradually during the reaction to keep the concentration of the cyclic diene low during the reaction. The reaction is continued until essentially all (at least 80%, preferably at least 95% and in particular at least 99%) of the calculated amount of cyclic diene has reacted.

The norbornene or substituted norbornene compounds obtained can be used for preparing polymers.

More specifically, in the present method, the cyclic diene is added gradually during the reaction.

The polymer according to the present invention is prepared by polymerizing a monomer prepared by the above described synthesis in the presence of a catalyst alone or in the presence of another monomer.

The present invention provides considerable advantages. The described method of the invention enables one to achieve a very pure product, high yield, short reaction time and, if desired, high concentrations of the exo diastereomer. Thus, after the reaction, the concentration of unreacted cyclic diene reactant in the reaction mixture is typically less than 3.0 wt-% and the concentration of the undesired trimer of the diene less than about 0.10 wt-%. It is even possible to achieve reaction mixtures that contain practically no residues of unreacted diene and no detectable amounts of trimer.

THE INVENTION

Within the scope of the present invention, the statement that a cyclic diene is introduced into the reaction "gradually", is understood in such a way that at least a part of the diene is reacted with an olefinic compound only after the reaction has already started. According to the invention, the cyclic diene, such as cyclopentadiene, formed in or before the reactor, is diluted in the reaction mixture and/or reacts so rapidly that dimerisation, trimerization, tetramerization and the like do not occur.

The present invention can be performed in a number of ways in accordance with its basic principles. Therefore, the preparation process may be a semi-batch or a continuous process, in which a cyclic diene is added as it is consumed in the reaction with an olefinic compound. A continuous process can be performed in, for example, an autoclave intended for continuous operation, a tube or loop reactor or in a cascade comprising any of these reactors. In a continuous process a cyclic diene is most preferably added evenly during the reaction, in order to provide a suitably low diene concentration. The addition of diene can, however, be increased or decreased (or even cut off temporarily) during the process to vary the diene concentration.

In a semi-batch process a diene is added as a function of time. In practice, a portion of the diene is first fed to the reactor together with an olefinic compound to form a reaction mixture, whereafter the rest of the diene is introduced into the reactor in one or more aliquots or as a continuous stream after the reaction has progressed for some time. Typically, the reaction is allowed to proceed for some tens of minutes before more diene is added into the reactor. This time is sufficient to allow about 1–90%, preferably about 5–80% and most preferably about 10–70%, of the diene to react to form norbornene or a norbornene derivative. The amount of added diene is typically equimolar with respect to the olefinic compound. In this case, the total amount of diene added to the reaction mixture at the beginning is most suitably less than equimolar with respect to the olefinic compound. According to one preferable alternative the molar ratio of the olefine and the diene is 51:49–99:1, preferably 55:45–90:10 and most preferably about 80:20–60:40, at the beginning of the reaction.

The reaction can be enhanced, in addition to the addition of diene, by controlling the reaction temperature and by selecting a suitable reaction system, in order to yield an end product of preferable composition. As shown in the Examples, by suitable selection of the ratio of the reagents and/or the reaction temperature, the yield and purity of the norbornene compound or the yield of the exo diastereomer of the norbornene compound or the yield of tetracyclododene can be maximized. Similarly, the ratio of the reagents, the reaction temperature and/or the reactor system can be selected in such a way that the time of synthesis is minimized and the rate of production is maximized.

The temperature can be controlled in alternative ways, such as forming a temperature ramp in a semi-batch process and arranging a temperature profile in a continuous process. In both of these cases the reaction temperature is typically 150–300° C., preferably about 160–250° C. and most preferably about 170–220° C. Less impurities are formed at lower temperatures but the time required for the synthesis is longer. The synthesis time can be shortened by elevating the temperature at the stage when the concentration of the cyclic diene is low, to obtain a small amount of impurities. For this reason, it is advantageous to use a low reaction temperature during the addition of the cyclic diene, whereafter the temperature is raised as the cyclic diene is used up. In this mode of operation, several successive temperature ramps may lie used in a semi-batch process, and accordingly, several successive temperature profiles may be used in a continuous process. The use of high temperatures with a low concentration of the cyclic diene makes it possible to use long synthesis times and to obtain more of the exo diastereomer of the monomer (for example, phenylnorbornene or indanylnorbornene) or more multicyclic monomers (for example, phenyl tetracyclododecene or benzofluorene), and yet very little of the harmful tricyclopentadiene.

The synthesis time can also be used to control the quality of the end product. Thus, when one wishes to maximize the yield of the monomer (such as phenylnorbornene or indanylnorbornene), the length of time required for synthesis is of the order of about 2 h, but when one wishes to maximize the amount of the exo diastereomer of the monomer or the amount of multicyclic monomer (such as phenyl tetracyclododecene or benzofluorene), the synthesis time is of the order of about 5 h.

In addition to the diene compound also the olefinic compounds, inhibitor or some other chemical compound to be introduced into the reaction mixture can be added as a function of time or into various parts of the reactor system in a manner described herein above. The solvent, olefinic component or some undesirable product component (especially, dimers, trimers and tetramers of cyclopentadiene) can be recycled and possibly cracked to improve conversion.

By the present invention it is possible to obtain reaction mixtures containing more than 80 wt-%, in particular over 83 wt-%, norbornene or its substituted derivatives and less than 3.0 wt-%, in particular less than 2.0 wt-%, of the cyclic diene. If desired, the proportion of the exo isomer can be increased to more than 10%, in particular more than 15% of the norbornene product. As example 7 shows, it is even possible to raise the proportion of the exo isomer to over 50%.

The amount of the undesired trimer can be reduced to less than 0.10 wt-%, in particular to less than 0.05 wt-% of the reaction mixture after the reaction.

The invention can be used to prepare norbornene and its substituted derivatives. When norbornene is prepared ethene is used as the olefinic reagent and dicyclopentadiene or cyclopentadiene is used as the cyclic diene. Most suitably dicyclopentadiene is cracked immediately before the reaction to form cyclopentadiene, for example, by feeding the reagent into the reaction mixture through a pipe with heated mantle.

When substituted norbornene derivatives are prepared, the suitable olefinic compounds include, for example, styrene, indene, alpha-olefines (such as 1-propene or 1-butene), cyclic olefines (such as cyclopentene or cyclohexene), linear dienes (especially 1,2-butadiene), acrylic acid and methacrylic acid and esters thereof (for example, methylacrylate), and unsaturated silanes (for example, vinyltrimethoxysilane) and the same cyclic dienes as described above.

The olefinic compounds described above, especially styrene and indene, act as the reaction medium at the same time, or in other words as the solvent for the cyclic diene. The cyclic diene also functions as an inhibitor (it prevents polymerization of the olefinic compound).

In a preferred embodiment, the diene introduced is dicyclopentadiene and it is added in such a way that it is cracked into cyclopentadiene immediately before the point of addition. In this case, it is most suitable to use a separate inhibitor (for example, 4-t-butylcatechol).

The purified or unpurified product that is prepared according to the method of this invention can be used to produce polymers by performing polymerization reactions of the monomer, in the presence of a metathesis catalyst, Ziegler-Natta catalyst, metallocene catalyst or the like, alone or together with an olefine or some suitable monomer. Thus, copolymers and terpolymers of the COC type can be prepared from phenylnorbornene by polymerizing the compound with olefines, especially with ethene, in the presence of metallocene catalysts. Crosslinked RIM-polymers, elastomers and COC polymers can be obtained from phenylnorbornene with metathesis catalysts. Corresponding products can be obtained from indanylnorbornene and norbornene. Ethylidenenorbornene is suitable for the preparation of EPDM elastomers. Methylacrylate substituted norbornene can be used to prepare the COC type polymers (arton) of Japan Synthetic Rubber in a ring-opening polymerization in the presence of metathesis catalysts. Trimethoxysilyl derivatives are suitable for the preparation of silane crosslinked EPDM elastomers.

The following examples are given to clarify the invention. Although a semi-batch process (where a cyclic diene is added at the beginning and once later on) is used for the sake of simplicity in the following illustrative examples, similar conditions (combination of cyclic diene/olefinic compound and temperature) can be achieved in a continuously operating process (single autoclave, tube or loop or any combination thereof in a cascade). Consequently, the examples are intended to be illustrative only and in no way restrictive of the invention.

In the following examples, the moment of starting the experiment has been defined as the moment at which heating of the reaction mixture is commenced.

EXAMPLE 1
(Semi-Batch)

Styrene and dicyclopentadiene (DCPD) of at least 95% purity were weighed into a reactor, in amounts corresponding to a molar ratio 76:24. 10 000 ppm of 97% pure 4-tert-butylcatechol were used to prevent oligomerisation reactions of the starting materials. Oxygen was removed from the reaction mixture prior to commencing the reaction by allowing nitrogen gas to pass through the mixture. Thereafter, the reaction mixture was heated to 180° C. and allowed to react for 4 hours, after which it was cooled to 30° C. 40 minutes after the start of the experiment pumping of DCPD into the reactor was commenced at a rate of 0.850 ml/min for 20 minutes. After the pumping had stopped, the molar ratio of the starting materials was 65:35. The composition of the oily, light yellowish reaction mixture is presented at various times after commencing the experiment in Table I.

TABLE I

Composition of the oily reaction product expressed as mass percentage at various times after commencing the experiment

| Time/min | 100 | 130 | 160 | 190 | 240 | 270 |
|---|---|---|---|---|---|---|
| Cyclopentadiene | — | — | — | — | — | — |
| Styrene | 13.89 | 10.05 | 9.68 | 9.02 | 10.03 | 3.12 |
| Dicyclopentadiene | 12.13 | 8.14 | 6.01 | 4.51 | 2.75 | 0.32 |
| phenylnorbornene | 73.98 | 81.56 | 83.22 | 84.33 | 83.82 | 88.49 |
| Tricyclopentadiene | — | — | — | — | — | — |
| Phenyltetracyclo-dodecene | — | 0.25 | 1.09 | 2.15 | 3.40 | 7.90 |
| Phenyltetracyclo-dodecene isomer | — | — | — | — | — | 0.16 |

Example 1 shows that by using the present method the fraction of phenylnorbornene in the product mixture is as high as 88.5% at its best, and that formation of adverse tricyclopentadiene is not detected at all. Tetracyclododecene formation begins only after 130 minutes after the start of the experiment and the formation of its isomer after 270 minutes. From the point of view of performing the steps for separation, the best moment to stop the reaction is at 120 minutes.

EXAMPLE 2
(Semi-Batch)

The same procedure as in Example 1 was carried out except that the pumping rate of DCPD was 0.900 ml/min and the pumping time 30 minutes. After the completion of pumping the molar ratio of the starting materials was 60:40. The composition of the oily, light yellowish reaction mixture is presented at various times after commencing the experiment in Table II.

TABLE II

Composition of the oily reaction product expressed as mass percentage at various times after commencing the experiment

| Time/min | 100 | 130 | 160 | 190 | 240 | 270 |
|---|---|---|---|---|---|---|
| Cyclopentadiene | — | — | — | — | — | — |
| Styrene | 10.06 | 6.19 | 5.44 | 5.12 | 4.17 | 1.17 |
| Dicyclopentadiene | 18.31 | 14.64 | 12.65 | 11.33 | 7.60 | 2.80 |
| Phenylnorbornene | 71.64 | 78.65 | 80.29 | 80.61 | 82.32 | 85.99 |
| Tricyclopentadiene | — | — | — | — | 0.09 | 0.28 |
| Phenyltetracyclo-dodecene | — | 0.52 | 1.62 | 2.93 | 5.82 | 9.55 |
| Phenyltetracyclo-dodecene isomer | — | — | — | — | — | 0.21 |

Example 2 shows that in this procedure the addition of DCPD was a little too excessive. This shows up as formation of adverse tricyclopentadiene at the end of the experiment. The fraction of tetracyclododecene is also slightly larger in this case.

EXAMPLE 3
(Semi-Batch)

The same procedure as in Example 1 was carried out except that the reaction mixture was heated to 200° C. and the pumping of DCPD was commenced 20 minutes after the start of the experiment. The composition of the oily, light yellowish reaction mixture is presented at various times after commencing the experiment in Table III.

TABLE III

Composition of the oily reaction product expressed as mass percentage at various times after commencing the experiment

| Time/min | 40 | 60 | 80 | 100 | 130 | 160 |
|---|---|---|---|---|---|---|
| Cyclopentadiene | 0.17 | 0.17 | — | — | — | — |
| Styrene | 27.33 | 15.32 | 8.02 | 6.54 | 9.16 | 12.86 |
| Dicyclopentadiene | 7.87 | 6.72 | 1.09 | 0.12 | — | — |
| Phenylnorbornene | 64.74 | 77.28 | 86.01 | 86.39 | 78.21 | 71.26 |
| Tricyclopentadiene | — | — | — | — | — | — |
| Phenyltetracyclo-dodecene | — | 0.51 | 4.83 | 6.95 | 11.30 | 13.60 |
| Phenyltetracyclo-dodecene isomer | — | — | 0.04 | 0.10 | 1.33 | 2.28 |

Example 3 shows that with the present method formation of the product is considerably more rapid. The fraction of phenylnorbornene in the product mixture is 86.4% at its best, and in addition to this, the formation of adverse tricyclopentadiene is not detected at all. However, tetracyclododecene begins to form already 60 minutes after the start of the experiment, and an isomer of this 80 minutes after the start. The product mixture remained fluid throughout the experiment, indicating that polystyrene was not formed to any adversely large amount during the reaction.

EXAMPLE 4
(Reference, Batch Process)

Styrene and dicyclopentadiene (DCPD), the purity of which was at least 95%, were weighed into a reactor in an amount corresponding to a molar ratio of 66:34. 10 000 ppm of 97% 4-tert-butylcatechol was used as an inhibitor to prevent oligomerization reactions of the starting materials. Before the reaction oxygen was removed from the reaction mixture by allowing nitrogen gas to pass through it. Thereafter, the reaction mixture was heated to 200° C. and allowed to react for 4 hours, after which it was cooled down to 30° C. The composition of the oily, light yellowish reaction mixture is presented at various times after commencing the experiment in Table IV.

TABLE IV

Composition of the oily reaction product expressed as mass percentage at various times after commencing the experiment

| Time/min | 20 | 30 | 40 | 60 | 80 | 100 |
|---|---|---|---|---|---|---|
| Cyclopentadiene | 1.85 | 0.90 | 0.93 | 0.14 | — | — |
| Styrene | 48.77 | 29.77 | 15.62 | 11.28 | 11.85 | 12.15 |
| Dicyclopentadiene | 27.70 | 15.17 | 5.76 | 1.91 | 0.65 | 0.19 |
| Phenylnorbornene | 21.68 | 53.90 | 76.47 | 80.53 | 75.60 | 71.12 |
| Tricyclopentadiene | — | — | — | 0.22 | 0.07 | 0.10 |
| Phenyltetracyclododecene | — | 0.26 | 1.22 | 5.57 | 10.26 | 13.73 |
| Phenyltetracyclododecene isomer | — | — | — | 0.35 | 1.57 | 2.71 |

Example 4 shows that with the reference method the fraction of phenylnorbornene in the product mixture is only 80.5% at its best, and the formation of adverse tricyclopentadiene begins to take place in varying amounts already after 60 minutes after the start of the experiment. Tetracyclododecene begins to form already 30 minutes after the start of the experiment and an isomer of this 60 minutes after the start. Additionally, as the experiment progresses the viscosity of the product mixture begins to increase, which results from the formation of polystyrene.

EXAMPLE 5
(Reference, Batch Process)

Styrene and dicyclopentadiene (DCPD), the purity of which was at least 95%, were weighed into a reactor in an amount corresponding to a molar ratio of 50:50. 10 000 ppm of 97% 4-tert-butylcatechol was used as an inhibitor to prevent oligomerisation reactions of the starting materials. Before the reaction oxygen was removed from the reaction mixture by allowing nitrogen gas to pass through it. Thereafter, the reaction mixture was heated to 170° C. and allowed to react for 130 minutes, after which it was cooled down to 30° C. The composition of the oily, light yellowish reaction mixture is presented at various times after commencing the experiment in Table V.

TABLE V

Composition of the oily reaction product expressed as mass percentage at various times after commencing the experiment

| Time/min | 15 | 20 | 30 | 40 | 60 | 80 | 100 | 130 | 160 |
|---|---|---|---|---|---|---|---|---|---|
| Cyclopentadiene | 8.16 | 1.03 | 0.30 | 0.13 | 0.04 | — | — | — | — |
| Styrene | 65.49 | 60.42 | 53.14 | 45.13 | 38.91 | 30.99 | 23.00 | 17.59 | 16.26 |
| Dicyclopentadiene | 19.80 | 25.54 | 23.70 | 21.80 | 17.71 | 13.36 | 9.65 | 6.61 | 5.76 |
| Phenylnorbornene | 6.54 | 13.01 | 22.87 | 29.94 | 43.34 | 55.65 | 67.35 | 75.80 | 77.98 |
| Tricyclopentadiene | — | — | — | — | — | — | — | — | — |
| Phenyltetracyclododecene | — | — | — | — | — | — | — | — | — |
| Phenyltetracyclododecene isomer | — | — | — | — | — | — | — | — | — |

Example 5 shows that with the batch method, in which cyclopentadiene and the olefinic compound are added in equimolar amounts at the beginning of the reaction, yields a rather impure reaction mixture that contains considerably large amounts of the olefinic starting material and dicyclopentadiene.

EXAMPLE 6
(Semi-Batch)

Indene and dicyclopentadiene (DCPD), the purity of which was at least 90%, were weighed into a reactor in amounts corresponding to a molar ratio of 69:31. 10 000 ppm of 97% 4-tert-butylcatechol was used as an inhibitor to prevent oligomerisation reactions of the starting materials. Before the reaction oxygen was removed from the reaction mixture by allowing nitrogen gas to pass through it. Thereafter, the reaction mixture was heated to 180° C. and allowed to react for 4 hours, after which it was cooled down to 30° C. 40 minutes after the start of the experiment DCPD was pumped into the reactor at a rate of 0.500 ml/min for 10 minutes. When the pumping was stopped the molar ratio of the starting materials was 65:35. The composition of the oily, dark yellowish reaction mixture is presented at various times after commencing the experiment in Table VI.

TABLE VI

Composition of the oily reaction product expressed as mass percentage at various times after commencing the experiment

| Time/min | 100 | 130 | 160 | 190 | 240 | 270 |
|---|---|---|---|---|---|---|
| Cyclopentadiene | 0.06 | — | — | — | — | — |
| Indene | 32.34 | 28.43 | 19.23 | 24.55 | 26.71 | 25.01 |
| Dicyclopentadiene | 6.02 | 3.19 | 1.47 | 0.03 | — | — |
| Endo indanylnorbornene | 53.58 | 58.52 | 67.92 | 61.88 | 58.53 | 57.60 |
| Exo indanylnorbornene | 8.00 | 9.84 | 10.17 | 12.63 | 12.89 | 14.48 |
| Tricyclopentadiene | — | — | 0.22 | — | — | — |
| Benzofluorene | — | 0.03 | 1.00 | 0.93 | 1.86 | 2.91 |
| Benzofluorene isomer | — | — | — | — | — | — |

Example 6 shows that with this method the fraction of indanylnorbornenes in the product mixture is 78.1% at 160 minutes after the experiment started. Although the yield remains modest, it is more important from the point of view of the use of the product that the adverse formation of tricyclopentadiene is not detected to any significant degree. Benzofluorene begins to form only at 130 minutes after the start of the experiment. For separation purposes, the most preferable moment to stop the reaction would be at 120 minutes.

EXAMPLE 7
(Semi-Batch)

The same procedure as in Example 6 was carried out except that the reaction mixture was heated to 200° C. and pumping of DCPD was commenced at 20 minutes after the start of the experiment. The composition of the oily, dark yellowish reaction mixture is presented at various times after commencing the experiment in Table VII.

TABLE VII

Composition of the oily reaction product expressed as mass percentage at various times after commencing the experiment

| Time/min | 40 | 60 | 80 | 100 | 130 | 160 |
|---|---|---|---|---|---|---|
| Cyclopentadiene | 0.79 | 0.02 | — | — | — | — |
| Indene | 40.41 | 36.67 | 33.46 | 36.02 | 31.71 | 47.30 |
| Dicyclopentadiene | 5.50 | 0.87 | 0.01 | — | — | — |
| Endo indanyl-norbornene | 44.67 | 49.56 | 48.31 | 41.83 | 39.01 | 21.81 |
| Exo indanyl-norbornene | 8.63 | 12.90 | 16.21 | 19.00 | 21.43 | 23.71 |
| Tricyclopentadiene | — | — | — | — | 0.14 | — |
| Benzofluorene | — | 0.20 | 2.01 | 3.07 | 6.05 | 5.33 |
| Benzofluorene isomer | — | — | — | 0.08 | 1.66 | 1.85 |

Example 7 shows indanylnorbornenes can be prepared faster with the method of the present invention, but the fraction of product in the product mixture is only 64.5% at its best. Furthermore, significant formation of adverse tricyclopentadiene cannot be detected at all. Benzofluorene begins to form at 60 minutes after the start of the reaction and an isomer of this at 100 minutes. The high temperature seems to favour, however, the formation of exo indanonorbornene.

EXAMPLE 8
(Reference, Batch Process)

Indene and dicyclopentadiene (DCPD), the purity of which was at least 90%, were weighed into a reactor in an amount corresponding to a molar ratio of 64:36. 10 000 ppm of 97% 4-tert-butylcatechol was used as an inhibitor to prevent oligomerisation reactions of the starting materials. Oxygen was removed from the reaction mixture prior to the reaction by allowing nitrogen gas to pass through it. Thereafter, the reaction mixture was heated to 180° C. and allowed to react for 4 hours, after which it was cooled down to 30° C. The composition of the oily, dark yellowish reaction mixture is presented at various times after commencing the experiment in Table VIII.

TABLE VIII

Composition of the oily reaction product expressed as mass percentage at various times after commencing the experiment

| Time/min | 60 | 80 | 100 | 130 | 160 | 190 | 270 |
|---|---|---|---|---|---|---|---|
| Cyclopentadiene | 0.06 | 0.03 | — | — | — | — | — |
| Indene | 47.18 | 35.64 | 27.43 | 25.38 | 22.98 | 21.72 | 23.74 |
| Dicyclopentadiene | 19.30 | 12.09 | 7.34 | 3.99 | 2.44 | 1.22 | — |
| Endo indanyl-norbornene | 29.31 | 45.62 | 57.27 | 60.59 | 64.15 | 61.85 | 55.16 |
| Exa indanyl-norbornene | 4.14 | 6.61 | 7.64 | 9.53 | 8.70 | 12.13 | 14.70 |
| Tricyclopentadiene | — | 0.01 | 0.17 | 0.17 | 0.36 | 0.32 | 0.39 |
| Benzofluorene | — | — | 0.15 | 0.34 | 1.37 | 2.75 | 5.62 |
| Benzofluorene isomer | — | — | — | — | — | — | 0.40 |

Example 8 shows that with this method the fraction of indanylnorbornene in the reaction mixture is 74.0% at its best at 190 minutes after the start of the experiment, but the formation of adverse tricyclopentadiene occurs in varying amounts already at 80 minutes. The formation of benzofluorene begins at 100 minutes after the start of the experiment and an isomer of this at 270 minutes.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

What is claimed is:

1. A method of producing a substituted derivative of norbornene by the Diels-Alder reaction, the method comprising:

reacting a cyclic diene selected from the group consisting of dicyclopentadiene and cyclopentadiene with an olefin compound selected from the group consisting of styrene and indene to yield the substituted norbornene derivative wherein the cyclic diene is added gradually during the reaction, the substituted derivative being phenyl norbornene or indanylnorbornene.

2. The method of claim 1 wherein the cyclic diene is dicyclopentadiene.

3. The method of claim 1 wherein the olefin compound is styrene.

4. The method claim 1 wherein the olefin compound is indene.

5. The method of claim 1 wherein the reaction is carried out as a continuous process or a semi-batch process, during which at least a fraction of the cyclic diene to be used is added subsequently to the start of the reaction.

6. The method of claim 1 wherein the molar ratio of the olefin compound and the cyclic diene at the beginning of the reaction is 51:49 to 99:1.

7. The method of claim 5 wherein the reaction is conducted at a temperature which is varied during the reaction.

8. The method of claim 7 wherein the ratio or the reagents and/or the temperature are controlled as a function of time in a batch or semi-batch method.

9. The method of claim 1 wherein the reaction temperature is 150–300° C.

10. The method of claim 7 wherein the ratio of the reagents and/or the reaction temperature are controlled in such a way that the yield and purity of the substituted norbornene derivative are as high as possible or the yield of the exo diastereomer of the substituted norbornene derivative or yield of tetracyclododecene is as high as possible.

11. The method of claim 1 wherein the cyclic diene is cyclopentadiene and said cyclic diene is obtained from dicyclopentadiene by cracking immediately prior to contacting the cycle diene with the olefin compound.

12. The method of claim 1 wherein the reaction is conducted in a reactor system and the ratio of the reagents and temperature are controlled at various points within the reactor system, said reactor system being optionally an operating autoclave, a tube, a loop or a cascade consisting of said reactors.

13. The method of claim 12 wherein the olefin compound is used as a reaction medium.

14. The method of claim 12 wherein the olefin compound, an inhibitor or a chemical reagent is added as a function of time or to various points of the reactor system.

15. The method of claim 12 wherein a solvent, the olefin compound or any other undesired product component is recycled and optionally cracked.

16. The method of claim 6 wherein the molar ratio is 55:45–90:10.

17. The method of claim 16 wherein the molar ratio is 80:20–60:40.

18. The method of claim 9 wherein the reaction temperature is 160 to 250° C.

19. The method of claim 18 wherein the reaction temperature is 170 to 220° C.

* * * * *